(12) United States Patent
Bowen

(10) Patent No.: US 9,150,666 B2
(45) Date of Patent: Oct. 6, 2015

(54) HYDROLYTICALLY STABLE, HYDROPHILIC ADHESION-PROMOTING MONOMERS AND POLYMERS MADE THEREFROM

(75) Inventor: Rafael L. Bowen, Gaithersburg, MD (US)

(73) Assignee: ADA Foundation, Chicago, IL (US)

( * ) Notice: Subject to any disclaimer, the term of this patent is extended or adjusted under 35 U.S.C. 154(b) by 746 days.

(21) Appl. No.: 12/360,421

(22) Filed: Jan. 27, 2009

(65) Prior Publication Data

US 2009/0188622 A1    Jul. 30, 2009

Related U.S. Application Data

(60) Provisional application No. 61/024,706, filed on Jan. 30, 2008.

(51) Int. Cl.
| | |
|---|---|
| *C08B 37/16* | (2006.01) |
| *C08B 11/18* | (2006.01) |
| *C08B 37/00* | (2006.01) |
| *C09J 4/00* | (2006.01) |
| *C09J 101/30* | (2006.01) |
| *A61K 6/08* | (2006.01) |
| *C08F 224/00* | (2006.01) |
| *C08L 5/16* | (2006.01) |

(52) U.S. Cl.
CPC .............. *C08B 37/0012* (2013.01); *A61K 6/08* (2013.01); *C08B 11/18* (2013.01); *C08B 37/0009* (2013.01); *C08F 224/00* (2013.01); *C08L 5/16* (2013.01); *C09J 4/00* (2013.01); *C09J 101/30* (2013.01)

(58) Field of Classification Search
CPC  C08B 37/0012; C08B 37/0009; C08B 11/18; C09J 4/00; C09J 101/30; C08L 5/16; C08F 224/00; A61K 6/08
See application file for complete search history.

(56) References Cited

U.S. PATENT DOCUMENTS

| | | |
|---|---|---|
| 3,066,112 A | 11/1962 | Bowen |
| 3,179,623 A | 4/1965 | Bowen |
| 3,194,783 A | 7/1965 | Bowen |
| 3,194,784 A | 7/1965 | Bowen |
| 4,707,558 A | 11/1987 | Wang et al. |
| 5,270,351 A | 12/1993 | Bowen |
| 5,320,886 A | 6/1994 | Bowen |
| 5,792,821 A | 8/1998 | Bowen |
| 5,910,551 A | 6/1999 | Bowen |
| 5,929,131 A | 7/1999 | Bowen |
| 5,981,740 A | 11/1999 | Bowen |
| 6,121,358 A | 9/2000 | Dershem et al. |
| 6,180,739 B1 | 1/2001 | Bowen |
| 6,583,248 B1 | 6/2003 | Bowen |
| 8,344,076 B2 * | 1/2013 | Dershem ................ 525/531 |

FOREIGN PATENT DOCUMENTS

| | | |
|---|---|---|
| EP | 1832617 A | 9/2007 |
| WO | WO9412540 | 6/1994 |
| WO | WO9625438 | 8/1996 |

OTHER PUBLICATIONS

Partial International Search Report, PCT/US2009/032200, filed Jan. 28, 2009, dated May 8, 2009, pp. 1-4.
Notification Concerning Transmittal of International Preliminary Report on Patentability of PCT/US2009/032200 dated Aug. 30, 2010.
International Search Report and the Written Opinion, International Application No. PCT/US2009/032200, Mailing Date Jun. 26, 2009.

* cited by examiner

*Primary Examiner* — Peter D Mulcahy
(74) *Attorney, Agent, or Firm* — Banner & Witcoff, Ltd.

(57) ABSTRACT

Disclosed are compositions that comprise vinylarylalkylene ethers of cyclodextrins optionally containing ether-linked adhesion-promoting groups, in combination with copolymerizable monomer or monomers. The copolymerizable monomer or monomers may include vinylarylalkylene ethers of oligohydroxy compounds (for example, sorbitol divinylbenzyl ether and others). The composition further may include stabilizers (for example, 1,3,5-trimethyl-2,4,6-tris(3,5-di-(tert)-butyl-4-hydroxybenzyl)benzene and others), and polymerization initiators (for example, phenylbis[2,4,6-trimethylbenzoyl]phosphine oxide and others) and reinforcing materials (for example, imogolite). Methods of preparing the compositions as well as the components of compositions and methods for their use in dental and other applications are also disclosed.

21 Claims, No Drawings

HYDROLYTICALLY STABLE, HYDROPHILIC ADHESION-PROMOTING MONOMERS AND POLYMERS MADE THEREFROM

GOVERNMENT INTEREST

This invention was supported in part by USPHS (NIDCR) Research grant 2 R01 DE005129-28 to the American Dental Association Foundation from the National Institute of Dental and Craniofacial Research, Bethesda, Md. The Government has certain rights in this invention. Disclaimer: Certain commercial materials and equipment are identified to specify experimental procedures. In no instance does such identification imply recommendation by NIST or the ADA Foundation or that the material identified is necessarily the best available for the purpose.

CROSS REFERENCE TO RELATED APPLICATIONS

This is a utility application based upon and referring to and incorporating by reference previously filed provisional Application Ser. No. 61/024,706 and entitled Hydrolytically Stable, Hydrophilic Adhesion-Promoting Monomers and Polymers Made Therefrom.

FIELD OF THE INVENTION

This invention relates to polymerizable compositions and to related methods. Some embodiments of this disclosed invention are of value in restorative dentistry, and in other biomedical and in industrial applications.

BACKGROUND OF THE INVENTION

American dentists spend much of their time restoring teeth that have developed secondary ("recurrent") caries at the margins of previous restorations. It is desirable to provide materials with which to restore teeth esthetically in a manner that will prevent formation of secondary caries caused by separation of restorative materials from tooth surfaces.

Desirably, a dental adhesive bonding material will, upon hardening, possess even higher strength of adhesion to the tooth surfaces than its strength of adhesion to itself (its cohesive strength). When mechanical, or polymerization shrinkage stress from the restorative material cause margin gap formation in the region of the adhesive-tooth interface, the gap should expose two surfaces within the synthetic (and ideally xenobiotic) cross-linked adhesive polymer, rather than a space between the adhesive polymer and the dentin or enamel. Cariogenic bacteria can thrive so long as dentin or enamel surfaces can buffer the acids they excrete, but could not survive within a polymeric enclosure in which their acids would lower the pH to levels below their tolerance.

Many conventional restorative materials and adhesive bonding compositions contain significant quantities of ester groups. The ester groups can be undesirable, in that such groups may become hydrolyzed or saponified in the harsh intraoral environment, especially at or near interfaces of the adhesive bonding compositions and the tooth surfaces. Opening of ester linkages can be catalyzed by acidic or basic aqueous conditions. In aqueous oral environments there are both fluctuations in pH and tensile stresses due to polymerization shrinkage and masticatory activity. Conventional dental resins and composite restorative materials undergo shrinkage during hardening (polymerization) and mechanical stresses from chewing and from thermal changes. Furthermore, human saliva contains esterases that can hydrolyze ester-containing compounds and composites: Finer, Y. Santerre, J. P. (2004), "Salivary esterase activity and its association with the biodegradation of dental composites," J Dent Res 83(1):22-26; Lee, Y. K., Powers, J. M. (2005), "Influence of salivary organic substances on the discoloration of esthetic dental materials—A review," J Biomed Mater Res Part B Appl Biomater 76B: 397-402; Lin, B. A., Jaffer, F., Duff, M. D., Tang, Y. W., Santerre, J. P. (2005), "Identifying enzyme activities within human saliva which are relevant to dental resin composite biodegradation," Biomaterials 4259-4264; and Santerre, J. P., Shajii, L., Tsang, H. (1999), "Biodegradation of commercial dental composites by cholesterol esterase," J Dent Res 78(8): 1459-1468. When subjected to mechanical stresses or thermal activity of restorative materials, conventional resin bonding agents can separate from the dentin or enamel forming a gap, which allows for "microleakage." Bacteria can grow in this gap, leading to staining and secondary ("recurrent") caries formation. Examples of ester-containing compositions are provided in U.S. Pat. No. 5,270,351 Adhesion-promoting agents incorporating polyvalent cations, U.S. Pat. No. 6,583,248 Polymerizable cyclodextrin derivatives, U.S. Pat. No. 6,180,739 Polymerizable cyclodextrin derivatives, U.S. Pat. No. 5,981,740 Polymerizable cyclodextrin derivatives for use in dental applications, U.S. Pat. No. 5,929,131 Polymerizable cyclodextrin derivatives, U.S. Pat. No. 5,910,551 Polymerizable cyclodextrin derivatives, U.S. Pat. No. 5,792,821 Polymerizable cyclodextrin derivatives, and U.S. Pat. No. 5,320,886 Hydrophilic crosslinking monomers and polymers made therefrom.

In some cases, the success of dental adhesive compositions used for bonding by prior and current methodologies is also limited, at least in part, because of partitioning or phase separations of the components as they diffuse into the substrate material: Spencer, P., Wang, Y. (2002), "Adhesive phase separation at the dentin interface under wet bonding conditions," J Biomed Mater Res 62(3):447-456. This partitioning or phase separation of components, which results from different solubility characteristics of the monomers, initiators, promoters, and other components of the compositions, separates components that must work together for optimal substrate interactions, polymerization, cross-linking, and durability of the adhesive bonding. Also, emphasis in recent research on adhesives for dental applications has been on the use of relatively hydrophobic monomers and their polymers to minimize subsequent water sorption: Tay, F. R., Pashley, D. H., Kapur, R. R., Carrilho, M. R. O., Hur, Y. B., Garrett, L. V., Tay, K. C. Y. (2007), "Bonding BisGMA to dentin—a proof of concept for hydrophobic dentin bonding," J Dent Res 86(11): 1034-1039. Examples of hydrophobic monomers and their polymers are described in Bowen, R. L. (1962): Dental Filling Material Comprising Vinyl Silane Treated Fused Silica and A Binder Consisting of the Reaction Product of Bis Phenol and Glycidyl Acrylate, U.S. Pat. No. 3,066,112; Bowen, R. L. (1965): Method of Preparing a Monomer Having Phenoxy and Methacrylate Groups Linked by Hydroxy Glycerol Groups, U.S. Pat. No. 3,179,623; Bowen, R. L. (1965): Silica-Resin Direct Filling Material and Method of Preparation, U.S. Pat. No. 3,194,783; and Bowen, R. L. (1965): Silica-Resin Direct Filling Material and Method of Preparation, U.S. Pat. No. 3,194,784. The industrial "vinyl ester resins," believed to have ensued therefrom, and most polyester resins, which polymerize by rapid free-radical mechanisms, do not adhere well to moist surfaces, or to hydrophilic substrates exposed to water. However, many important structural polymers (collagen, cellulose, etc.), minerals (calcium phosphates), and many structural industrial substrates (oxidized or anodized metals or their alloys, hardened cement aggregates, etc.) are hydrophilic and are hydrated when in typical environments. There has been concern expressed in prior art regarding the effects of water sorption: Ito S, et al., 2005, "Effects of resin hydrophilicity on water sorption and changes in modulus of elasticity," *Biomaterials* 26:6449-6459. Water sorption into hydrophilic resins (polymers) consisting of chains linked or cross-linked with hydrolyzable ester [—C(=O)O—C—] groups are not expected to be durable in harsh environments for prolonged periods of time. In adhesion-promoting applications, water solubility of the monomeric formulation components is desired to enable penetration, attachment and three-dimensional interlinking with hydrated substrates. This is especially desirable for dental adhesive-bonding compositions, Asmussen, E., Hanson, E. K., Peutzfeldt, A. (1991), "Influence of the solubility parameter of intermediary resin on the effectiveness of the Gluma bonding system," *J Dent Res* 70:1290-1293. The concern expressed in prior art regarding water sorption of adhesive polymers, Ito, S., Hashimoto, M., Wadgaonkar, B., Svizero, N., Carvalho, R. M., Yiu, C., Rueggeberg, F. A., Foulger, S., Saito, T., Nishitani, Y., Yoshiyama, M., Tay, F. R., Pashley, D. H. (2005), "Effects of resin hydrophilicity on water sorption and changes in modulus of elasticity," *Biomaterials* 26:6449-6459, is related to degradation that can occur from hydrolysis of ester linkages within inadequately cross-linked structures of the prior art polymers.

The prepolymerization components of the dental adhesive bonding material should be sufficiently hydrophilic to penetrate, interlink with and form maximally strong interfacial attractive interactions with the hydrophilic components of tooth structures. The components of the dental adhesive bonding material should be sufficiently compatible with one another and with water to prevent phase separations during countercurrent diffusion into the hydrated asperities of tooth surfaces. The components of the dental adhesive bonding material should not be susceptible to degradation via hydrolysis of ester bonds either before or after polymerization. The components of the dental adhesive bonding material should form a densely cross-linked polymer when hardening in situ.

It would desirable to provide substantially anhydrous monomer formulations that have high solubility parameters of their components to obtain penetration, attachment, and three-dimensional interlinking with the hydrated collagenous assemblages that give strength to tendons, ligaments, bones and teeth, with the micropores of hydrated biological minerals, and with hydrated polysaccharide assemblages that are important in both plant and animal structures, and which formulation components can polymerize to form hydrolytically stable, densely cross-linked polymers. The invention seeks in some embodiments to provide materials with some or all of these properties.

SUMMARY

Generally, the invention provides, in one of the embodiments, a composition that includes polymerizable cyclodextrin derivatives normally in combination with reactive diluent copolymerizable monomer(s); stabilizers that comprise polymerization inhibitors, antioxidants, and selected sequestering compounds for metallic ions that can catalyze oxidation; polymerization initiator(s); and other types of ingredients. In other embodiments, the invention provides lower-molecular-weight comonomers described herein wherein the formulations may contain little or none of the polymerizable cyclodextrin derivatives. Other types of ingredients also may be used to adjust the viscosity and other properties of the formulations containing the polymerizable cyclodextrin derivatives described herein and to facilitate specific intended methods of applying the formulations to the specific intended substrates.

The polymerizable cyclodextrin derivatives and reactive diluent comonomers, the latter also referred to herein as copolymerizable monomer or monomers and as reactive copolymerizable monomers, composed of lower-molecular-weight molecules, are both preferably derivatized with polymerizable vinylarylalkylene groups that are connected to their backbone moieties via ether linkages. In some embodiments, the cyclodextrins and reactive diluent copolymerizable monomer or monomers contain ether-linked vinylbenzyl groups.

In other embodiments the polymerizable cyclodextrins and reactive diluent comonomers or copolymerizable monomer or monomers are prepared by reactions comprising the use of vinylarylalkylene halides, vinylarylalkylene tosylates or vinylarylalkylene moieties containing other facile leaving groups. The useful halides comprise chloride, bromide, and iodide. Such reagents may be selected from the group comprising para-vinylbenzyl halide or tosylate, meta-vinylbenzyl halide or tosylate, ortho-vinylbenzyl halide or tosylate, 1-vinyl-naphthalene-4-methyl halide or tosylate (1-vinyl-4-methylenenaphthalene halide or tosylate), 4-vinyl-3-chlorobenzyl halide or tosylate, 2-vinyl-4-methoxybenzyl halide or tosylate, 2-vinyl-4-phenoxybenzyl halide or tosylate, o-methyl styrene halide or tosylate (o-styrenemethyl halide or tosylate), 1-methylene-2-vinylnaphthalene halide or tosylate, 2-methylene-1-vinylnaphthalene halide or tosylate, 1-methylene-5-vinylnaphthalene halide or tosylate, and 2-vinyl-1-biphenylmethyl halide or tosylate. Said halides comprise chloride, bromide, and iodide, with the iodides providing the most facile leaving group of these halides. In one embodiment, wherein the desired one or more vinylarylalkylene halide(s) are available only as a chloride or bromide, sodium or other alkaline iodide is added to the $S_N2$ reaction medium to reversibly exchange with the chloride or bromide on the vinylarylalkylene reagent(s) to facilitate the desired ether-forming reactions.

Other embodiments comprise the desired bimolecular nucleophilic substitution ($S_N2$) ether-forming reactions of these reagents with hydroxyl groups of mixtures of beta-cyclodextrin, alpha-cyclodextrin, gamma-cyclodextrin, dihydroxy compounds, sugar alcohols, and other oligohydroxy compounds.

In addition to the vinylarylalkylene substituent groups, in some embodiments the cyclodextrin(s), sugar alcohol(s), and oligohydroxy compound(s) are further derivatized to attach one or more ether-linked adhesion-promoting groups, sometimes referred to as "ligand" groups to the molecules. The adhesion-promoting groups may be selected from the group comprising carboxyl-containing groups, amide-containing groups, amide-attached amino acid groups, ether-linked oligopeptide-containing groups, amide-attached oligopeptide groups, and aldehyde-containing groups, and wherein the linkage consists of from 1-16 carbon atoms. It is believed that the presence of such hydrophilic ligand groups, together with residual hydroxyl groups, will promote adhesion to hydrophilic surfaces such as those of dentin, enamel, and appropriate biological and industrial materials.

The reactive diluent comonomers or copolymerizable monomer(s) comprise one or more types of compounds substantially all of which contain one or more copolymerizable functional group(s) capable of reacting with the same or other copolymerizable monomer(s) and also with derivatized copolymerizable cyclodextrin(s) to form densely cross-linked copolymers. The copolymerizable monomer(s) that contain two or more vinylarylalkylene groups on each molecule increase the density of cross-linking when copolymerizing with the same or other copolymerizable monomer(s) and with derivatized cyclodextrin(s) to form copolymers. The cyclodextrin derivatives may be present in any appropriate amount relative to the amount of the derivatized copolymerizable sugar alcohol(s), copolymerizable mono- di- tri- and oligo-ethylene glycols, and other derivatized copolymerizable oligohydroxy compound(s).

In some embodiments, one or more reactive diluent comonomers containing only one methacrylate or acrylate group per molecule may be used to obtain the desired viscosity of the composition. However, comonomers containing more than one methacrylate or acrylate group per molecule may be but preferably are not used because of the potential for subsequent lessening of cross-link density due to hydrolysis of their ester groups. Preferred monomers described herein containing more than one polymerizable or copolymerizable group per molecule have their polymerizable groups connected with linkages that are chemically and hydrolytically stable to enable high cross-link density and to maintain durable cross-link density in the resulting polymer(s).

For reducing the intrinsic viscosity of the polymerizable cyclodextrin derivatives, the polymerizable cyclodextrin derivatives together with the reactive diluent comonomers, or these comonomers not containing the polymerizable cyclodextrin derivatives, the other types of ingredients may comprise an inert solvent or fluid agents to form a substantially homogenous fluid mixture or solution of the ingredients in the composition. It is preferred to incorporate only the minimal amounts necessary of relatively inert fluids, which may comprise, for example, acetone, ethanol, isopropyl and other lower-alkyl alcohols, dimethyl sulfoxide, tetramethylene sulfoxide, tetrahydrofuran, tetramethylene sulfone, and others. The fluid agents are preferably substantially removed from the compositions by means of evaporation, diffusion, or fragmentation before or during the application and polymerization of the compositions.

In one embodiment, the invention includes a hydrolytically stable, adhesion-promoting monomeric composition that does not require the incorporation of cyclodextrin derivatives, which composition may contain one or more polymerizable vinylarylalkylene group selected from the group comprising para-vinylbenzyl, meta-vinylbenzyl, ortho-vinylbenzyl, 1-vinyl-naphthalene-4-methyl, 4-vinyl-3-chlorobenzyl, 2-vinyl-4-methoxybenzyl, 2-vinyl-4-phenoxybenzyl, ortho-methyl styrene, 1-methylene-2-vinylnaphthalene, 2-methylene-1-vinylnaphthalene, 1-methylene-5-vinylnaphthalene, and 2-vinyl-1-biphenylmethyl groups connected to their backbone moieties via ether linkages, wherein the backbone moieties may comprise derivatized sugar alcohols, ethyleneglycol, diethyleneglycol, triethylene glycol, oligo-ethylene glycols, sorbitol, and other derivatized oligohydroxy compounds thereby forming reactive copolymerizable monomers, and these said reactive copolymerizable monomers may be further derivatized with one or more ether-linked adhesion-promoting ligand groups selected from the group comprising undissociated carboxyl groups, dissociated anions of carboxyl groups, amides of carboxyl groups, amide-containing groups, amide-attached amino acid groups, ether-linked oligopeptide-containing groups, amide-attached oligopeptide groups, and aldehyde-containing groups. This composition should contain at least one stabilizer such as one or more selected from the group comprising di-tert-butyl sulfide, the monomethyl ether of hydroquinone, 4-tert-butyl-catechol, butylated hydroxytoluene, butylated hydroxyanisole, 4-tert-butylcatechol, ascorbic acid, ascorbic acid salts, ascorbic acid anionic derivatives, 1,3,5-trimethyl-2,4,6-tris (3,5-di-t-butyl-4-hydroxybenzyl)benzene, ethylenediaminetetraacidic acid, salts of ethylenediaminetetraacidic acid, anionic derivatives of ethylenediaminetetraacidic acid, phytic acid, salts of phytic acid, anionic derivatives of phytic acid, oxalic acid, salts of oxalic acid, anionic derivatives of oxalic acid, citric acid, citric acid salts, and anionic derivatives of citric acid, and before use in bonding applications this composition should contain a polymerization initiator such as, for example at least one selected from the group comprising phenylbis(2,4,6-trimethylbenzoyl)phosphineoxide, camphorquinone, camphorquinone-10-sulfonic acid, a salt of N-vinylarylalkylene-N-phenylglycine, a salt of N-vinylarylalkylene-N-tolylglycine, a salt of N-vinylarylalkylene-N-methylglycine, ethyl-4-dimethylaminobenzoate, diphenyliodoniumhexafluorophosphate, benzoyl peroxide, N,N-dihydroxyethyl-para-toluidine, 4-dimethylaminophenethylalcohol, 3-dimethylaminobenzoic acid, p-toluenesulfinic acid lithium salt, p-toluenesulfinic acid sodium salt hydrate, phenacylpyridiniumoxalate, 1-phenacylpyridinium bromide, phenacyltriphenylphosphonium bromide, 3,3'-carbonylbis [7-(diethylamino)coumarin], meso-tetraphenylporphine, benzene-1,2,4,5-tetracarboxylic diimide, naphthalene diimide, 2,2'-azo-bis(amidinopropane) 2(HCl), N,N'-bis-vinlbenzyl-1,4,5,8-naphthalenediimide, 2-benzoylmethylene-1-methyl-beta-naphthothiazoline, and water-soluble derivatives thereof. Furthermore, such a composition may optionally contain one or more reinforcing material, and relatively inert solvents that can be substantially removed from the composition before polymerization of the composition.

The polymerizable cyclodextrin derivatives combined with the reactive diluent copolymerization monomer or monomers may be used in various dental and non-dental applications. In some embodiments, it is contemplated that the composition may comprise one or more said reactive diluent comonomers or copolymerizable monomers in which the composition does not contain cyclodextrin derivatives. Also, in some embodiments, it is contemplated that the composition may be employed in preventive dental applications such as protective coatings and as sealants for obturating development pits, fissures, and the minute defects referred to as "white spots" to prevent the development of caries (dental cavities).

It is essential that all compositions described herein be tested and/or otherwise evaluated in a manner that assures their safety for use in dental, biomedical, or industrial applications as appropriate.

The compositions further may include other components, such as polymerization initiators, stabilizers to prevent oxidation or premature polymerization during storage, antimicrobial agents, fluoride-releasing agents, reinforcing materials and inert volatile solvents used to adjust the viscosity and other properties of the formulations to be used to facilitate specific intended properties and methods of applying the formulations to the specific intended substrates. These ingredients may be present in any amount relative to one another appropriate to provide the intended functional property of the component.

In one embodiment, a mixture of alpha-cyclodextrin, beta-cyclodextrin, and gamma-cyclodextrin are derivatized to contain ether-linked vinylbenzyl groups on substantially every molecule by reacting said cyclodextrins with vinylbenzylhalide reagent molecules substantially in excess of the reactive hydroxyl groups contained in the cyclodextrins, with the reactions being catalyzed by a compound selected from the group consisting of DBU (1,8-diazabicyclo[5.4.0]undec-7- ene), 1,4-diazabicyclo[2.2.2]octane, hexamethylenetetramine, N,N-di-isopropyl ethylamine, triethylamine, tripropylamine, tributylamine, N,N-dimethylbenzylamine, tribenzylamine, N,N,N',N'-tetramethyl-1,4-phenylenediamine, N,N-dimethylaniline, triphenylamine, pyridine, poly(4-vinylpyridine), sodium-tert-butoxide, cross-linked poly(4-vinylpyridine), 4-(dimethylamino)pyridine, triphenylantimony, triphenylphosphine, oxides of Li, Na, K, Rb, Cs, Mg, Ca, Sr, Ba, La, hydroxides of Li, Na, K, Rb, Cs, Mg, Ca, Sr, Ba, La, carbonates of Li, Na, K, Rb, Cs, bromides of Li, Na, K, Rb, Cs, Mg, Ca, Sr, Ba, La, iodides of Li, Na, K, Rb, Cs, Mg, Ca, Sr, Ba, La, and mixtures thereof.

In another embodiment, the invention provides a kit. The kit includes one or more containers or dispensers. The containers or dispensers may contain or provide means of applying formulations containing polymerizable cyclodextrin derivatives, copolymerizable monomers, stabilizers, polymerization initiators, antimicrobial agents, fluoride-releasing agents, reinforcing agents, and other types of ingredients. Alternatively, a kit may provide means of conveying one or more of the formulation components separated within a kit. The provision of separated components within one or more kits allows the materials to be transported and to remain stable or unreacted until used. The containers or dispensers of the polymerizable components should preferably not be absent of or completely impermeable to the oxygen of atmospheric air, so that phenolic-type stabilizers, such as are exemplified hereinafter, will be and will remain effective.

In another embodiment, the invention provides methods for bonding together surfaces of solid or semisolid objects and the preparation of protective coatings for use on solid or semisolid surfaces. Compositions described herein may be applied to one or more said surfaces as neat liquids, solutions in volatile solvents, semisolid and/or liquid components applied sequentially by means of applicator instruments, brushes, sprayers, syringes, or other means known to those skilled in the art. Generally, the invention comprises applying to one or more surfaces a composition that includes one or more reactive polymerizable monomer or monomers and appropriately selected components as described herein. The applying of the composition may be accomplished by applying a formulation containing a previously prepared mixture of all of the components, one or more of the components and then applying one or more of the other components to a surface, or by applying one or more of the components to one of the surfaces and then applying one or more of the other components to the other surface of the two surfaces to be bonded together, or the components of the composition may be combined just prior to application to one surface to be coated or to two or more surfaces to be joined. Examples include but are not limited to application to tooth surfaces as a protective coating alone or as an adhesive for maintaining adherence of an overlying layer of a protective coating material, attachments of orthodontic brackets to tooth surfaces, attachments of inlays, crowns, and bridges to appropriately prepared teeth, fixation of prosthetic or orthopedic devices to bone and/or other biological tissue surfaces, bonding together biomaterials, attachment of two materials used in industry, and joining together surfaces of solid or semisolid objects in an aqueous environment.

In another embodiment, a method for preparing a derivatized copolymerizable cyclodextrin is provided wherein substantially every cyclodextrin molecule contains at least one copolymerizable substituent. The method includes derivatizing a cyclodextrin in a derivatization reaction, such as those described in the Examples detailed hereinafter. In some embodiments of these examples, the derivatization reactions may be catalyzed with one or more members selected from the group consisting of: NaBr, NaI, DBU (1,8-diazabicyclo[5.4.0]undec-7-ene), 1,4-diazabicyclo[2.2.2]octane, hexamethylenetetramine, N,N-di-isopropyl ethylamine, triethylamine, tripropylamine, tributylamine, N,N-dimethylbenzylamine, tribenzylamine, N,N,N',N'-tetramethyl-1,4-phenylenediamine, N,N-dimethylaniline, triphenylamine, pyridine, poly(4-vinylpyridine), sodium-tert-butoxide, cross-linked poly(4-vinylpyridine), 4-(dimethylamino)pyridine, triphenylantimony, triphenylphosphine, oxides of Li, Na, K, Rb, Cs, Mg, Ca, Sr, Ba, or La, hydroxides of Li, Na, K, Rb, Cs, Mg, Ca, Sr, Ba, or La, carbonates of Li, Na, K, Rb, Cs, and mixtures thereof.

In another embodiment, a method for preparing derivatized cyclodextrin is provided. Compositions containing one or more alpha-cyclodextrin, beta-cyclodextrin, and gamma-cyclodextrin derivatives can be prepared by bimolecular nucleophilic substitution ($S_N2$) ether-forming reactions, well known to those skilled in the art, of vinylarylalkylene halides or vinylarylalkylene tosylates with said cyclodextrins to form the desired derivatives. These vinylarylalkylene halides or vinylarylalkylene tosylates can be selected from the group consisting of para-vinylbenzyl halide or tosylate, meta-vinylbenzyl halide or tosylate, ortho-vinylbenzyl halide or tosylate, 1-vinyl-naphthalene-4-methyl halide or tosylate (1-vinyl-4-methylenenaphthalene halide or tosylate), 4-vinyl-3-chlorobenzyl halide or tosylate, 2-vinyl-4-methoxybenzyl halide or tosylate, 2-vinyl-4-phenoxybenzyl halide or tosylate, o-methyl styrene halide or tosylate (o-styrenemethyl halide or tosylate), 1-methylene-2-vinylnaphthalene halide or tosylate, 2-methylene-1-vinylnaphthalene halide or tosylate, 1-methylene-5-vinylnaphthalene halide or tosylate, and 2-vinyl-1-biphenylmethyl halide or tosylate, wherein para-vinylbenzyl halide or tosylate, and/or meta-vinylbenzyl halide or tosylate are preferred, and wherein said vinylarylmethylene ether groups can be obtained by bimolecular nucleophilic substitution ($S_N2$) reactions of one or more of the corresponding vinylarylalkylenehalides or vinylarylalkylenetosylates with nucleophilically activated hydroxyl groups of said cyclodextrins. Said halides comprise Cl, Br, and I, wherein the iodide is the preferred halide because it is the most facile leaving group of these halides and can be formed by exchange with the other halides by incorporation of an alkaline element halide such as sodium iodide into the reaction mixtures.

In another embodiment, a substantial portion of the cyclodextrin molecules, each of which contain substantially one or more ether-attached polymerizable groups, also contain one or more covalently attached ether-linked adhesion-promoting groups (also known as ligand groups). Said adhesion-promoting groups may comprise alkyl, aryl, and/or alkyl-aryl groups that may contain one or more undissociated carboxyl groups, dissociated anions of said carboxyl groups, amides of said carboxyl groups, aldehyde groups, nitrogen-containing groups, amine-containing groups, or other polar or ionic groups. Said adhesion-promoting groups may be attached by means of bimolecular nucleophilic substitution ($S_N2$) reactions of one or more reagents. Examples of such reagents include but are not limited to those selected from the group consisting of 2-haloacetic acid, 3-halopropionic acid, 4-halobutyric acid, 5-halovaleric acid, 6-halocaproic acid, 7-enanthic acid, 8-halocaprylic acid, 9-halopelargonic acid, 10-halocapric acid, 12-halolauric acid, 16-halopalmitic acid, 2-halopropionamide, 4-halobutanal, 5-halopentanal, 6-halohexanal, 6-(halomethyl)uracil, 2-(halomethyl)pyridine, 3-(halomethyl)pyridine, 4-(halomethyl)pyridine, 4-(halomethyl)benzoic acid, 3-(halomethyl)benzoic acid, and 4-vinyl- 3-carboxybenzylhalide. In the foregoing, halo or halide refer to chloro or chloride, bromo or bromide, or iodo or iodide.

DESCRIPTION OF CERTAIN EMBODIMENTS

Numerous properties are desired of an adhesive, caries-preventive, or restorative material. In certain embodiments, a composition will form an adhesive, caries-preventive, or restorative material that has one or more of the following properties. Nonetheless, it should be understood that the compositions and kits of the claimed invention are not in all embodiments intended to be limited to dental restorative use, but to the contrary, it is envisioned that the compositions and kits will have other biological, biomedical, commercial, and industrial applications. Likewise, it should be understood that the invention is not limited by the description of desired properties, and that it is possible for the appended claims to cover subject matter that does not possess the desired properties.

An adhesive composition should cause interfacial binding interactions by competing with water that may be present on or within the surface (particularly when the composition is applied in vivo) to imbibe and displace water from substrate sites on or within the surface(s), thereupon forming a densely linked, cross-linked, and with some types of substrates, a substrate-interlinked polymeric structure. In the most preferred embodiments, the composition is free or at least essentially free of ester groups. In some embodiments, however, ester groups may be present, especially in diluent (viscosity lowering) monofunctional comonomers that are not involved in cross-linking during polymerization of the formulations. The composition should be hydrophilic and compatible with other natural and synthetic polymers and substrates expected to be encountered. The composition is preferably in an anhydrous form or a substantially anhydrous form when applied. Finally, the components of the composition should be compatible with one another and should have similar solubility characteristics, such that separation is avoided or minimized during diffusive interactions with the substrates and the "setting" (polymerization) of the composition.

Especially when used as a dental adhesive bonding agent, the polymerized composition preferably should have an adhesive strength that is greater than the cohesive strength of the material, such that, should the material be subjected to excessive stresses, any exposed gap will expose two surfaces of polymer rather than a space between polymer and dentin, enamel or other substrate surface. Cariogenic bacteria can thrive as long as dentin or enamel can buffer the acids they excrete, but could not survive or cause secondary caries when disposed within an intrapolyermeric gap in which the acids they generate will lower the pH to levels below their tolerance. The polymerized composition should have cohesive and adhesive bond strengths sufficient for use in the intended application, one of which is as an adhesive for dental restorations. By analogy in certain industrial applications, adhesive strength to substrates greater than cohesive strength of the bonding polymer might protect the substrates from corrosion or other forms of degradation.

For many applications, the composition prior to setting (polymerization) includes a derivatized cyclodextrin. Cyclodextrins are cyclic oligosaccharides composed of five or more alpha-D glucopyranoside units linked via alpha-1,4 linkages. Cyclodextrins are commercially available, typically in several configurations including alpha-cyclodextrin (composed of six glucopyranoside units), beta-cyclodextrin (composed of seven glucopyranoside units), and gamma-cyclodextrins (composed of eight glucopyranoside units). In some embodiments, mixtures of derivatized alpha-, beta-, and gamma-cyclodextrin are employed.

The cyclodextrins are preferably derivatized at least with ether-linked vinylarylalkylene groups. In one embodiment, the invention provides a method for preparing cyclodextrins derivatized with vinylarylmethylene groups, the method including derivatizing the cyclodextrins. The vinylarylmethylene groups are attached via ether linkages resulting from substitution of hydroxyl (—OH) groups on the cyclodextrin. For example, vinylbenzylchloride, vinylbenzylbromide, and vinylbenzyliodide, which fall within the category of vinylarylmethylene reagents, may be reacted with a cyclodextrin to cause the cyclodextrin to become derivatized. The cyclodextrin molecules may be derivatized with ether-linked vinylarylalkylene groups alone or to an extent suitable for further derivatization with other types of reagents, which depends upon the desired properties of the final formulation(s). For instance, anywhere from about 5% to about 66%, preferably about 19% to about 38%, and more preferably about 14% to about 24% of the hydroxyl groups originally present on individual cyclodextrin molecules may be substituted to form vinylarylalkylene ether groups.

In preparing the derivatized cyclodextrins in some embodiments, the reactions are catalyzed with one or more materials. Catalysts may include NaBr, NaI, DBU (1,8-diazabicyclo[5.4.0]undec-7-ene), 1,4-diazabicyclo[2.2.2]octane, hexamethylenetetramine, N,N-di-isopropyl ethylamine, triethylamine, tripropylamine, tributylamine, N,N-dimethylbenzylamine, tribenzylamine, N,N,N',N'-tetramethyl-1,4-phenylenediamine, N,N-dimethylaniline, triphenylamine, pyridine, poly(vinylpyridine), cross-linked poly(4-vinylpyridine), sodium tert-butoxide, 4-(dimethylamino)pyridine, triphenylantimony, triphenylphosphine, oxides of Li, Na, K, Rb, Cs, Mg, Ca, Sr, Ba, or La, hydroxides of Li, Na, K, Rb, Cs, Mg, Ca, Sr, Ba, or La, carbonates of Li, Na, K, Rb, Cs, and mixtures thereof. The alkylene portion of the reagent may have any suitable number of carbon atoms, generally from 1 to 10 carbon atoms. The vinyl portion should be connected directly to the aromatic moiety of the vinylarylalkylene group.

The cyclodextrin optionally may be further derivatized with an ether-linked adhesion-promoting group. In one embodiment, this adhesion-promoting group includes ether-linked groups having from 2 to 16 carbon atoms. For example, the cyclodextrin may be further derivatized with the use of one or more reagents selected from the group comprising haloacetic acid, 2-haloethanoic acid, 3-halopropionic acid, 3-halopropanoic acid, 4-halobutyric acid, 4-halobutanoic acid, 5-halopentanoic acid, 6-halohexanoic acid, 6-halocaproic acid, 7-haloheptanoic acid, 8-halooctanoic acid, 9-halononanoic acid, 10-halodecanoic acid, 12-halododecanoic acid, 16-halohexadecanoic acid, 2-halo-propionamide, omega-halo alkyl, aryl, and/or alkyl-aryl group(s) containing amide-attached amino acid groups, amide-attached oligopeptide groups, 4-halobutanal, 5-halopentanal, 6-halohexanal, 6-(halomethyl)uracil, picolylhalide, 4-(halomethyl)benzoic acid, 3-(halomethyl)benzoic acid, 2-(halomethyl)pyridine, 3-(halomethyl)pyridine, 4-(halomethyl)pyridine, and 4-vinyl-3-carboxybenzylhalide as reagents for attaching adhesion-promoting groups to cyclodextrins derivatized with one or more vinylarylmethylene groups. Mixtures thereof may be used. In the foregoing, halo or halide refer to chloro or chloride, bromo or bromide, or iodo or iodide.

Vinylbenzyl chloride is available from numerous suppliers, including for example Dow Corporation under the product designation "VBC." Vinylbenzyl chloride can be obtained as a mixture of 57% meta-isomer and 43% para-isomer or as a reagent comprising the para-isomer as the major component. It is contemplated that the ortho isomer of vinylbenzyl chloride also may be employed. More generally, when vinylbenzyl chloride, bromide, or iodide is employed, the desired isomeric ratios may be utilized. The iodide constitutes the most facile leaving group of these halides and can be formed by exchange with the chloride by reaction with an alkaline element halide, an example of which is sodium iodide.

The preferred composition further includes one or more reactive copolymerizable monomer or monomers. The reactive copolymerizable monomer or monomers may comprise any suitable monomer that is compatible with the derivatized cyclodextrin. In some embodiments, the copolymerizable monomer or monomers are biologically compatible or dentally compatible. Generally, the monomer includes at least one copolymerizable unsaturated functional group and it may include plural copolymerizable unsaturated functional groups.

The invention also provides in certain embodiments a composition comprising:

one or more copolymerizable monomer or monomers in which said composition does not contain cyclodextrin derivatives, wherein said composition does contain at least one copolymerizable monomer having two or more ether-linked vinylbenzyl groups, wherein said composition also contains at least one copolymerizable monomer having at least one ether-linked vinylbenzyl group and also one or more ether-linked groups selected from the group consisting of carboxyl-containing groups, amide-containing groups, amide-attached amino acid groups, amide-attached oligopeptide groups, and aldehyde-containing groups, wherein the linkage consists of from 1-16 carbon atoms, wherein said composition also contains at least one stabilizer, and one or more polymerization initiator(s).

Especially in dental and biological applications, the copolymerizable monomer or monomers are appropriately selected and capable of reacting with or without the derivatized cyclodextrins to form biologically compatible reaction products.

In a preferred embodiment, the copolymerizable monomer or monomers contain one or more vinylarylalkyl ether group(s) substituted on each molecule of one or more sugar alcohols and oligohydroxy compounds such as, for example, sorbitol (gulcitol), allitol (allodulcitol), epi-fucitol (6-deoxyglucitol), meso-erythritol, dulcitol (galacitol), iditol (1,2,3,4,5,6-hexane hexol), perseitol (mannoheptitol), gulitol, gulonic gamma-lactone talitol (altritol, talaite), xylitol, ribitol, erythrose, allose, arabitol, galactose, gluco-heptose, gluco-methylose (isorhamnose), glucose (dextrose), gulose, idose, isomalt, lactitol, mannitol (mannite, acritol), mannoheptose, mannose, maltitol, ribose, talose, xylose, epi-fucose (quinovose), psicose (allulose), idonic acid (2,3,4,5,6-pentahydroxy hexanoic acid), mannuronic acid, talonic acid, galacturonic acid, rhamnitol (rhamnite), ethyleneglycol, diethyleneglycol, triethyleneglycol, tetraethyleneglycol, poly(ethyleneglycol) (200), poly(ethyleneglycol)(400), poly(ethyleneglycol) (1000), glycerol, tetrahydrofurfuryl alcohol, isobornyl alcohol, and 2-hydroxyethyl phosphate. The reactive copolymerizable monomer or monomers may also be based on 4-O-beta-D-galactopyranosyl-alpha-D-glucopyranose, beta-D-fructofuranosyl-alpha-D-glucopyranoside, and methyl 4-O-beta-D-galactopyranosyl-alpha-D-glucopyranoside, and trisaccharides such as alpha-cellotriose (O-beta-D-glucopyranosyl-(1-4)-O-beta-D-glucopyranosyl-(1-4)-alpha-D-glucopyranose), alpha-maltotriose, raffinose, gentianose and other saccharides, wherein hydroxyl groups of said oligohydroxy compound(s) are substituted by reaction(s) with vinylarylalkylene halides or vinylarylalkylene tosylates such as those selected from the group consisting of para-vinylbenzyl halide or tosylate, meta-vinylbenzyl halide or tosylate, ortho-vinylbenzyl halide or tosylate, 1-vinylnaphthalene-4-methyl halide or tosylate (1-vinyl-4-methylenenaphthalene halide or tosylate), 4-vinyl-3-chlorobenzyl halide or tosylate, 2-vinyl-4-methoxybenzyl halide or tosylate, 2-vinyl-4-phenoxybenzyl halide or tosylate, o-methyl styrene halide or tosylate (o-styrenemethyl halide or tosylate), 1-methylene-2-vinylnaphthalene halide or tosylate, 2-methylene-1-vinylnaphthalene halide or tosylate, 1-methylene-5-vinylnaphthalene halide or tosylate, and 2-vinyl-1-biphenylmethyl halide or tosylate. The desired hydroxyl groups of said oligohydroxy compounds, which compounds are to become copolymerizable monomer or monomers, may be substituted with the use of a reagent such as a vinylarylalkylene halide, such as a chloride, bromide, or iodide, but preferably not fluoride, or with a vinylarylalkylene tosylate, or with a vinylarylalkylene reagent containing another leaving group effective to facilitate the desired bimolecular nucleophilic substitution ($S_N2$) reactions. The substitution reaction may employ one mole of such vinylarylmethylene reagents per mole of a monohydroxy or dihydroxy compound, two moles of such vinylarylmethylene reagents with oligohydroxy compounds that contain 3 to 6 hydroxy groups, and three to four moles of such vinylarylmethylene reagents with oligohydroxy compounds that contain more than 6 hydroxyl groups. Generally, the copolymerizable monomer or monomers may contain any suitable number of copolymerizable groups. In addition thereto, said reactive diluent comonomers may contain monomers having only one polymerizable vinyl group per molecule. Reactive diluent comonomers substituted with a methacrylate or acrylate group should preferably have only one such copolymerizable group per molecule. Examples are, for instance, glycerolmonomethacrylate, methylmethacrylate, hydroxypropylmethacrylate, hydroxyethylmethacrylate and the like. For other than dental or biological applications, the reactive diluent comonomer or comonomers may comprise styrene, divinylbenzene, ring-substituted styrenes, and other monomers that are capable of reacting with the derivatized cyclodextrins, if appropriately utilized.

In addition to containing at least one unsaturated functional group, the reactive diluent comonomers or reactive copolymerizable monomer or monomers may be derivatized to contain one or more ether-linked adhesion-promoting group(s) in which the connecting linkage to the adhesion-promoting group(s) comprises one or more, preferably 1 to 16 carbon atoms, wherein the connecting linkages are comprised of alkyl, aryl, and/or alkyl-aryl group(s). The adhesion-promoting group(s) may comprise one or more undissociated carboxyl groups, dissociated anions of carboxyl groups, amides of carboxyl groups, amide-attached amino acid groups, amide-attached oligopeptide groups, aldehyde groups and groups obtained by use of the following reagents. These said ether-linked adhesion-promoting group(s) may be obtained by bimolecular nucleophilic substitution ($S_N2$) reactions of one or more ionized hydroxyl group(s) with reagents selected from the group comprising, for example, 2-haloacetic acid, 2-haloethanoic acid, 3-halopropionic acid, 3-halopropanoic acid, 4-halobutyric acid, 4-halobutanoic acid, 5-halopentanoic acid, 6-halohexanoic acid, 6-halocaproic acid, 7-haloheptanoic acid, 8-halooctanoic acid, 9-halononanoic acid, 10-halodecanoic acid, 12-halododecanoic acid, 16-halohexadecanoic acid, 2-halo-propionamide, omega-halo alkyl, aryl, and/or alkyl-aryl group(s) containing amide-attached amino acid groups, amide-attached oligopeptide groups, 4-halobutanal, 5-halopentanal, 6-halohexanal, 6-(halomethyl)uracil, picolylhalide, 4-(halomethyl)benzoic acid, 3-(halomethyl) benzoic acid, and 4-vinyl-3-carboxybenzylhalide, and mixtures thereof, wherein the halogen atom(s), signified by "halo," are selected from the group consisting of chlorine, bromine, and iodine. To the extent that ester formation might accompany the formation of the ether attachments of these groups, the esters can be hydrolyzed to the extent desired. It is contemplated that mixtures of different copolymerizable monomer or monomers and cyclodextrins may be employed. When so substituted, the copolymerizable monomer or monomers may be substituted to any suitable extent.

The substitution reactions of the oligohydroxy compounds to form the one or more said reactive diluent comonomers or reactive copolymerizable monomer derivatives may be catalyzed by the use of DBU (1,8-diazabicyclo[5.4.0]undec-7-ene), 1,4-diazabicyclo[2.2.2]octane, hexamethylenetetramine, N,N-di-isopropyl ethylamine, triethylamine, tripropylamine, tributylamine, N,N-dimethylbenzylamine, tribenzylamine, N,N,N',N'-tetramethyl-1,4-phenylenediamine, N,N-dimethylaniline, triphenylamine, pyridine, poly (4-vinylpyridine), sodium-tert-butoxide, cross-linked poly (4-vinylpyridine), 4-(dimethylamino)pyridine, triphenylantimony, triphenylphosphine, oxides of Li, Na, K, Rb, Cs, Mg, Ca, Sr, Ba, or La, hydroxides of Li, Na, K, Rb, Cs, Mg, Ca, Sr, Ba, or La, carbonates of Li, Na, K, Rb, Cs, and mixtures thereof.

In practice, it is believed that the derivatization of a cyclodextrin in accordance with the foregoing teachings will provide a variety of derivatized cyclodextrin products with a large number of permutations of positional arrangements of substituent groups on cyclodextrin molecules and a large variety of spatial configurations. This is believed to be desirable to allow for favorable "docking" or binding interactions with the high diversity of "receptor sites" on biological substrates such as dentin, which three-dimensional computer modeling and other sources of information have divulged.

Generally, the composition may include other ingredients such as a polymerization initiator, a stabilizer, and one or more reinforcing materials comprising solid particles and/or fibers of suitably small dimensions. These materials may be present in any amounts suitable for their intended purposes. With regard to the polymerization initiator, this may be any suitable material, including, for instance, a photoinitiator, a chemical-cure initiator, or a dual-cure polymerization initiator. Exemplary initiators include, for instance, a phenyl bis(2, 4,6-trimethylbenzoyl)phosphine oxide, camphorquinone, camphorquinone-10-sulfonic acid, a salt of N-vinylarylalkylene-N-phenylglycine, a salt of N-vinylarylalkylene-N-tolylglycine, a salt of N-vinylarylalkylene-N-methylglycine, ethyl-4-dimethylaminobenzoate, diphenyliodonium-hexafluorophosphate, benzoyl peroxide, N,N-dihydroxy-ethyl-para-toluidine, 4-dimethylaminophenethylalcohol, 3-dimethylaminobenzoic acid, p-toluenesulfinic acid lithium salt, p-toluenesulfinic acid sodium salt hydrate, phenacylpyridiniumoxalate, 1-phenacylpyridinium bromide, phenacyltriphenylphosphonium bromide, 3,3'-carbonylbis[7-(diethylamino)coumarin], meso-tetraphenylporphine, benzene-1,2, 4,5-tetracarboxylic diimide, naphthalene diimide, 2,2'-azobis(amidinopropane) 2(HCl), N,N'-bis-vinlbenzyl-1,4,5,8-naphthalenediimide, 2-benzoylmethylene-1-methyl-beta-naphthothiazoline, water-soluble derivatives thereof, and mixtures thereof. The polymerization initiators should have solubility characteristics that are favorable for use in combination with the other components of the composition. For instance, the polymerization initiator should be completely soluble in the other components of the composition. One suitable photoinitiator, phenylbis[2,4,6-trimethylbenzoyl] phosphine oxide, is sold as IRGACURE 819 by Ciba Specialty Chemicals Products. Some organophilic initiators may reversibly form complexes with said polymerizable cyclodextrin derivatives thereby rendering them completely soluble in the other components of the composition and sufficiently soluble in water at 20° C. to 40° C.

With regard to said stabilizers, any suitable stabilizer or combination of stabilizers may be employed that will prevent oxidation, discoloration or premature polymerization of the monomeric components of the formulations. Molecular oxygen is a diradical that rapidly combines with carbon radicals of prematurely initiated monomer molecules. Sterically hindered phenolic stabilizers cannot do that, but can donate hydrogen atoms to the peroxy radicals so formed, thereby converting the latter to much more stable hydroperoxide groups. Said stabilizers may include, for instance, di-tert-butyl sulfide, the monomethyl ether of hydroquinone, 4-tert-butylcatechol, butylated hydroxytoluene, butylated hydroxyanisole, 4-tert-butylcatechol, ascorbic acid and its salts or anionic derivatives, the antioxidant 1,3,5-trimethyl-2,4,6-tris(3,5-di-t-butyl-4-hydroxybenzyl)benzene, available from suppliers such as Ciba Specialty Chemicals Products as IRGANOX 1330, sequestering compounds for undesirable metallic ions (that could catalyze oxidation or prematurely initiate polymerization) EDTA (ethylenediaminetetraacidic acid and its salts or anionic derivatives), phytic acid and its salts or anionic derivatives, oxalic acid and its salts or anionic derivatives, citric acid and its salts or anionic derivatives, and mixtures thereof.

With regard to the reinforcing material, any suitable material may be employed that will enhance the characteristics of the compositions. Exemplary materials include, for instance, silica-containing glasses, condensates, precipitates, or fibers of appropriate dimensions for the intended end use. For application to dentin, the reinforcing materials should be comminuted if necessary to reduce their longest dimensions to be predominately less than one micrometer so as to not block passage of the accompanying monomers into dentinal tubules. One preferred material is imogolite, an aluminum silicate mineral principally derived from volcanic ash or by synthetic methods known to those skilled in the art. Generally, the reinforcing aggregate materials should be coated with a reactive material that promotes interfacial bonding with the polymerizable cyclodextrin derivatives and the copolymerizable monomer or monomers. For instance, the aggregate material may be coated with a silane coupling agent containing copolymerizable vinyl groups, such as, for example, styrylethyltrimethoxysilane, methacryloxypropyltrimethoxysilane and others, which, together with means of applying said coatings are well known to those skilled in the art.

In particular, a preferred reinforcing material comprises particles of imogolite that have been comminuted to the desired length, which for use on tooth surfaces is predominately less than one micrometer, and have had their surfaces substantially coated with one or more silane coupling agents such as, for example, vinylbenzylaminotrimethoxysilane, vinyltrimethoxysilane, styrylethyltrimethoxysilane, and/or methacryloxypropyltrimethoxysilane. Especially preferred are said imogolite particles treated with a combination of styrylethyltrimethoxysilane together with an approximately equal amount of octyltrimethoxysilane. Silane agents are applied to imogolite particles in a polar, volatile solvent at a nominal pH of about 3.5 to 4.0 and sonicated or vigorously agitated, which substantially minimizes clustering and aggregation of the individual imogolite particles, which particles are electrically neutral at a pH of about 8.4, and maximizes uniform coating of these particles. The thusly treated imogolite particles are then blended into the reaction products with forced evaporation of the solvent before, during, or after blending into the monomer formulations. The vinyl groups of the styrylethyltrimethoxysilane or other silanes containing vinyl groups, on the surfaces of the very small elongated imogolite particles or other said reinforcing material are beneficial for subsequent copolymerization with and reinforcement of the adhesion-promoting compositions. The combined use of an alkyl silane, such as for example octyltrimethoxysilane, is beneficial for preventing or reducing clustering or aggregation and improving dispersion of individual particles within the monomeric formulations and the polymers made therefrom. Such surface-treated imogolite "nano-rods," which consist of fiber-like microscopic particles of an aluminum silicate mineral, when adequately dispersed in these adhesive monomeric formulations, are expected to result in reinforced polymers with increased fracture toughness.

In some embodiments, the components of the composition are provided in the form of one or more kits. An individual kit may contain only portions of the components of the composition or all of the components of the composition together with other objects or materials. The kit optionally further may be provided with one or more tools for introducing the composition to a surface.

In use, the heretofore described compositions may be used in any suitable application. It is not necessary that the composition be applied in a dental environment, but to the contrary in some embodiments it is contemplated that the composition may be employed in a different biological, commercial or industrial application. Generally, for dental uses the compositions are provided and applied for use within a human oral cavity. For a prosthetic or cosmetic application, the compositions are provided and may be applied externally in a manner and amount that are effective to obtain the desired results. The composition may be applied in a single-composition treatment, but need not be so applied. For instance, in some embodiments, other compositions, such as surface preparatory materials or post-application materials, may be provided in addition to the composition of the invention, either before or after application of the inventive composition as is appropriate.

To provide such materials, it is necessary to recognize the complexity of the chemical properties of such surfaces. And for practical applications, specific surfaces must be treated with adhesive bonding compositions that contain molecules having accessible functional groups that can readily form attractive interactions with the atomic and molecular species of these surfaces. The adhesion-promoting molecules should comprise a comparable complexity of chemical and physical characteristics to interact optimally with the chemical and physical complexities of the substrate surfaces. Fortunately, due to the rapid translational and rotational movements of molecules in solution, an appropriately complex mixture of adhesion-promoting molecules can undergo a "natural selection" of collisional binding interactions of particular molecules with receptive sites on complex substrate surfaces. As interfaces become covered with these selected copolymerizable molecules, the remaining polyfunctional monomers can fill the intervening spaces. Copolymerization can then occur, uniting the adsorbed surface-bound monomeric molecules and monomers in the spaces between the surfaces to be connected, resulting in strong bonding with densely cross-linked polymer.

Accordingly, it is useful to determine structure-property relationships and solubility parameters of such components with the use of 3-D computer-modeling software (such as, for example, a Computer-Aided Chemistry facility like CAChe 6.1.1 WorkSystem Pro including BioMedCAChe, Fujitsu Ltd., Beaverton, Oreg.), and then by way of a SMILES (Simplified Molecular Input Line Entry Specification, or a simplified subset thereof) algorithm, translating information regarding these components into an application for calculating solubility parameters (such as, for example, Hoy Solubility Parameter Calculator, developed by Computer Chemistry Consultancy). Therewith, a desirable ratio of the number of hydrophobic vinyl-containing moieties to the number of hydrophilic ligand plus residual hydroxyl groups on the derivatized cyclodextrins and copolymerizable molecules can be predicted. Such predictions are used to adjust the proportions of reagents during the syntheses of the various monomers to provide miscibility, compatibility, avoidance of phase separation, and affinity for substrate surfaces of the formulation components before and during polymerization of the monomers in situ.

The following Examples are provided to illustrate certain embodiments of the invention. These Examples are not intended to limit the scope of the application.

EXAMPLES

Example 1

Beta-cyclodextrin (BCD) was derivatized to form a product having multiple polymerizable groups and also multiple ionizable adhesion-promoting groups, each attached with ether linkages. Matrix Assisted Laser Desorption/Ionization-Time Of Flight Mass Spectrometry (MALDI-TOF MS) provided evidence of the number and type of the attached groups. Recrystallized and dried beta-cyclodextrin was heated at about 60° C. for four days in an aqueous solution of calcium hydroxide plus potassium hydroxide (pH about 13) after addition of a polymerization stabilizer (1,3,5-trimethyl-2,4,6-tris(3,5-di-(tert)-butyl-4-hydroxybenzyl)benzene, and 6 moles of vinylbenzyl chloride plus 15 moles of potassium 6-bromohexanoate per mol of BCD. MALDI-TOF MS spectra of reaction products were obtained with a Bruker Reflex II™ mass spectrometer and were obtained during and after the synthesis. Preliminary analyses indicated that the derivatized cyclodextrin family contained a large number of different combinations of derivatives. The MALDI-TOF-MS peaks corresponded to various numbers of vinylbenzyl and hexanoate substituents per molecule. This synthesis produced derivatizations of up to seven of the 21 hydroxyl groups of BCD with both polymerizable and adhesion-promoting groups on most molecules. It was reasonable to expect that within many of the MALDI-TOF-MS peaks (representing combinations of substituents) there were also many positional arrangements (permutations) of the polymerizable and adhesion-promoting groups on the derivatized BCD molecules. This indicated that there was a very large variety of spatial configurations within this family of reaction products.

Example 2

A composition was formulated by combining some of the derivatized cyclodextrins described in Example 1 with commercially available sorbitol dimethacrylate. A portion (0.0419 g) of the derivatized cyclodextrins was mixed with sorbitol dimethacrylate (0.3261 g) and methacrylic acid (0.2383 g) as reactive diluents to provide a fluid viscosity. Phenylbis[2,4,6-trimethylbenzoyl]phosphine oxide (also known as IRGACURE 819) (0.0271 g) was added as a photoinitiator. Formulation 1 had retained a very small amount of the stabilizer 1,3,5-trimethyl-2,4,6-tris(3,5-di-(tert)-butyl-4-hydroxybenzyl)benzene, (also known as 3,3',3",5,5',5"-hexa-tert-butyl-alpha,alpha',alpha"-(mesitylene-2,4,6-triyl)tri-p-cresol and as IRGANOX 1330). The stabilizers contained in the sorbitol dimethacrylate and methacrylic acid as received were also present in this composition.

The composition described in Example 2 was used to evaluated its effectiveness as an adhesive for bonding a dental composite material to human dentine in extracted teeth, by the method described in Example 3 herein below, in comparison with the compositions described in the following Comparative Examples.

Comparative Example 1

A composition similar to that of Example 2 was prepared, except that the derivatized cyclodextrins were omitted. This formulation contained 0.3261 g of SDM2, 0.2383 g of MAA, 0.0271 g of Phenylbis[2,4,6-trimethylbenzoyl]phosphine oxide (IRGACURE 819), and the same small amount of 1,3,5-trimethyl-2,4,6-tris(3,5-di-(tert)-butyl-4-hydroxybenzyl)benzene, (also known as 3,3',3",5,5',5"-hexa-tert-butyl-alpha,alpha',alpha"-(mesitylene-2,4,6-triyl)tri-p-cresol and as IRGANOX 1330) and the stabilizers contained in the sorbitol dimethacrylate and methacrylic acid as received.

Comparative Example 2

A commercially-available self-etching primer bonding system was obtained. Components listed in a Material Safety Data Sheet for this product included "Silanated colloidal silica, sodium fluoride, bisphenol A diglycidylmethacrylate, 2-hydroxyethyl methacrylate, hydrophobic dimethacrylate, 10-methacryloyloxydecyl dihydrogen phosphate, N,N-diethanol-p-toluidine, and d,l-camphorquinone."

Example 3

Test Methods Used in Evaluating Formulations as Adhesives

The products of Comparative Examples 1 and 2 and of Example 2 were evaluated as follows: Ground mid-coronal flat human dentin surfaces were used for all of the formulations. For Comparative Example 1 and Example 2, the surfaces were etched with 37% aqueous phosphoric acid for 15 seconds and rinsed with distilled water for 10 seconds. Formulations were applied to these moist dentin surfaces and light-cured for 10 seconds. A packable composite was applied to the primed surfaces through irises and light-cured for 60 seconds. The manufacturer's instructions were followed for the formulation of Comparative Example 2. The bonded samples were all stored in water for 24 hours before the bonds were tested by loading to failure in a shearing orientation. A holding device was used to evaluate the shear bond strengths (SBS). The stainless-steel ring containing the dentin-bonded composite within its iris was placed against a vertical surface of a nylon block. The ring and the composite were sheared off, at a crosshead speed of 0.5 mm/min, with a flat chisel pressing against the edge of stainless-steel the ring close to the tooth surface. The flat chisel was connected to the platen of a Universal Testing Machine (Instron Corp., Canton Mass., USA).

One-way ANOVA was performed on the data. The average (n=6) values of Shear Bond Strengths (SBS), as measured in Example 3, were defined as the loads at fracture divided by the 4 mm diameter iris opening areas were, in megaPascals (MPa):

Example 2: SBS=24.6 MPa (standard deviation=5.4 MPa).

Comparative Example 1: SBS=13.2 MPa (standard deviation=3.7 MPa).

Comparative Example 2: SBS=17.4 MPa (standard deviation=4.0 MPa).

The shear bond strength of samples utilizing the formulation of Example 2 was significantly higher ($p<0.05$) than those of the Comparative Examples 1 and 2.

Example 3

Sorbitol dimethacrylate containing about 0.67 mole percent of phenylbis[2,4,6-trimethylbenzoyl]phosphine oxide (IRGACURE 819) was applied to dentin surfaces after the surfaces had been etched, rinsed, and excess water removed as described in Example 3 above. The testing procedure was also the same as in Example 3, except that n=3. This was to confirm that bond-strength values of Example 2 were reproducible.

Example 4

The formulation and testing procedure were the same as in Example 2 except that after the excess water was removed from the surfaces, 200-proof ethanol was applied to the dentin surfaces with a brush-tipped applicator for 10 s to replace much of the surface water with alcohol (Tay, F. R., Pashley, D. H., Kapur, R. R., Carrilho, M. R. O., Hur, Y. B., Garrett, L. V., Tay, K. C. Y. (2007), "Bonding BisGMA to dentin—a proof of concept for hydrophobic dentin binding," *J Dent Res* 86(11): 1034-1039), and n=3. This was to see if the effect of ethanol pretreatment would increase the bond-strength values obtained by one of these hydrophilic formulations as much as had been reported in these references wherein relatively hydrophobic formulations had been used.

Individual SBS values were as follows: Example 4 had none that fell within the ranges of those of 2 or 4. The individual SBS values were all within the range of those of Comparative Example 1.

Example 5

Aliquot 1

Sorbitol divinylbenzyl ether was synthesized as follows. Into a mechanically stirred reaction vessel, 368 g of sorbitol (2.02 moles); 2 L of DMSO (also known as dimethyl sulfoxide, methyl sulfoxide, sulfinylbismethane) (28.2 moles); 319.56 g of pyridine (4.04 moles); 20 g of 1,4-diazabicyclo[2.2.2]octane, (also known as triethylenediamine, TEDA and Dabco™) (0.18 moles); 1 g of 1,3,5-trimethyl-2,4,6-tris(3,5-di-(tert)-butyl-4-hydroxybenzyl)benzene, (also known as 3,3',3",5,5',5"-hexa-tert-butyl-alpha,alpha',alpha"-(mesitylene-2,4,6-triyl)tri-p-cresol and as IRGANOX 1330); (0.0013 mole) were placed.

Then 0.2 g of 4-tert-butylcatechol (also known as 4-tert-butylpyrocatechol) (0.0012 mole) was dissolved in 617 g (4.04 moles) of freshly distilled vinylbenzylchloride, and this solution was added over a period of 3 to 4 h with occasional cooling because the reactions were slightly exothermic. These components were then stirred at room temperature for 16 hours. After suction filtration (no solids were seen on the filter), about 90-92% of the DMSO was removed by distillation with use of a strong vacuum at 25-30 degrees Celsius. Then 1.5 L of ether was added and stirred for 30 min to remove DMSO and pyridine salts. The ether layer was removed by decantation. This was done 3 times. Then the ether was evaporated with use of a rotary evaporator and strong vacuum. After removal of the ether, one-third of the fluid product still containing some DMSO was put aside. This portion will be designated "Aliquot 1" herein.

Example 5

Aliquot 2

To the other two-thirds of the sorbitol divinylbenzyl ether (herein designated as "Aliquot 2"), 1 L of acetone was added, and stirred for 30 min before decanting the acetone layer. This was done 3 times. Then when removing the acetone with use of the rotary evaporator and a strong vacuum gelation occurred, resulting in a very viscous product into which a strong glass rod could be moved about, but samples were difficult to remove because of a coherent "memory" of the gel. This gelation was thought to be due to extraction (removal) of the stabilizers by the acetone washing and/or depletion of sufficient oxygen, which is required for the stabilizers to be effective. The additional inventive syntheses described hereunder assure maintenance of adequate concentrations of the stabilizers and oxygen that is contained in air.

Example 6

A method for synthesis of derivatized cyclodextrin is as follows. Into a mechanically stirred reaction vessel supplied with an eluting atmosphere of dried and filtered air, are placed 567.49 g of recrystallized and dried beta-cyclodextrin (0.50 mole); 10.5 moles of pyridine; and one or more strong basic catalysts, as needed, selected from 0.50 mole of 1,4-diazabicyclo[2.2.2]octane (also known as triethylenediamine, TEDA, and DABCO), 0.50 mole of 1,8-diazabicyclo[5.4.0]undec-7-ene (DBU), and 4-(dimethylamino)pyridine; together with 0.167 mole of a stabilizer such as 1,3,5-trimethyl-2,4,6-tris(3,5-di-(tert)-butyl-4-hydroxybenzyl)benzene (also known as 3,3',3",5,5',5"-hexa-tert-butyl-alpha,alpha',alpha"-(mesitylene-2,4,6-triyl)tri-p-cresol, and as IRGANOX 1330). A minimal amount, if any, of DMSO (also known as dimethyl sulfoxide, methyl sulfoxide, sulfinylbismethane) and/or one or more other inert aprotic polar solvents such as, for example, tetrahydrofuran (THF), acetone, tetramethylene sulfone, tetramethylene sulfoxide, N,N-dimethylformamide, acetonitrile, pyridine are added only if needed to form a substantially homogenous fluid mixture or solution of these said ingredients that stirs easily or is capable of being stirred. (The least toxic and most volatile and easiest to remove effective solvents and catalysts are, of course, preferred.) Then with continued stirring, 4.00 moles of vinylbenzylchloride, vinylbenzylbromide, or vinylbenzyliodide is slowly added with occasional cooling if necessary to maintain the temperature below about 30 degrees Celsius over a period of 3 to 4 hours, or slowly heated to no more than about 50 degrees Celsius until analytic monitoring indicates that the etherification reactions are complete. Vinylbenzyliodide is preferred because the iodide constitutes the most facile leaving group of these halides and can be formed by exchange with the other halides by incorporation of an alkaline element halide such as sodium iodide into the reaction mixtures.

Then with continued stirring, 6.50 moles of 6-bromohexanoic acid, dissolved in a minimal amount of DMSO to make a clear fluid solution, is added slowly (with occasional cooling if necessary to maintain the temperature below about 30 degrees Celsius) over a period of 3 to 4 hours, or slowly heated to no more than about 50 degrees Celsius until analytic monitoring indicates that the etherification reactions are complete.

Then stabilizers such as, for example, 0.2 g of 4-tert-butylcatechol (also known as 4-tert-butylpyrocatechol) (0.0012 mole) and 1 g (0.0013 mole) of 1,3,5-trimethyl-2,4,6-tris(3,5-di-(tert)-butyl-4-hydroxybenzyl)benzene, (also known as 3,3',3",5,5',5"-hexa-tert-butyl-alpha,alpha',alpha"-(mesitylene-2,4,6-triyl)tri-p-cresol and as IRGANOX 1330) are added and thoroughly mixed with the reaction products. The reaction products are supplied with an atmosphere of dried and filtered air. After suction filtration (if indicated), 1.5 L of ether is added and stirred for 30 min to remove amine salts and undesired solvents. The ether layer is removed by decantation. This is done 3 times. Then the ether is evaporated with stirring under an eluting current of dried and filtered air. After removal of the ether, 1 L of acetone is added, and stirred for 30 min before the acetone layer is decanted. This is done 3 times. Then stabilizers such as, for example, 0.2 g of 4-tert-butylcatechol (also known as 4-tert-butylpyrocatechol) (0.0012 mole) and 1 g (0.0013 mole) of 1,3,5-trimethyl-2,4,6-tris(3,5-di-(tert)-butyl-4-hydroxybenzyl)benzene, (also known as 3,3',3",5,5',5"-hexa-tert-butyl-alpha,alpha',alpha"-(mesitylene-2,4,6-triyl)tri-p-cresol and as IRGANOX 1330) are added and thoroughly mixed with the reaction products, because the stabilizers previously added might have been substantially removed by the extractive washings with ether and acetone. The reaction products are supplied with an atmosphere of dried and filtered air; the oxygen in air is necessary for the stabilizers to be effective.

For derivatization of alpha-cyclodextrin, which has 18 hydroxyl groups, and for derivatization of gamma-cyclodextrin, which has 24 hydroxyl groups, the relative proportions of a vinylarylmethylenehalide and of adhesion-promoting reagents are adjusted proportionally relative to the concentrations used with beta-cyclodextrin, which has 21 hydroxyl groups. The other components and procedures also are adjusted.

Example 7

Sorbitol vinylarylmethylene ethers are synthesized as follows. Into a mechanically stirred reaction vessel supplied with an atmosphere of dried and filtered air, 368 g of sorbitol (2.02 moles); 319.56 g of pyridine (4.04 moles); 20 g of 1,4-diazabicyclo[2.2.2]octane, (also known as triethylenediamine, TEDA, and DABCO) (0.18 moles); and a stabilizer such as 1 g of 1,3,5-trimethyl-2,4,6-tris(3,5-di-(tert)-butyl-4-hydroxybenzyl)benzene, (also known as 3,3',3",5,5',5"-hexa-tert-butyl-alpha,alpha',alpha"-(mesitylene-2,4,6-triyl)tri-p-cresol, and as IRGANOX 1330); (0.0013 mole) are placed. Optionally, a stabilizer such as butylated hydroxytoluene (also known as 2,6-di-tert-butyl-4-methylphenol) (0.0013 mole) can be used. A minimal amount, if any, DMSO (also known as dimethyl sulfoxide, methyl sulfoxide, sulfinylbismethane) is added only if needed to form a substantially homogenous fluid mixture or solution of these said ingredients that stirs easily or is capable of being stirred. Then with continued stirring, 4.04 moles of vinylbenzylchloride, vinylbenzylbromide, or vinylbenzyliodide is slowly added. The vinylbenzyliodide can be formed by incorporation of an alkaline element iodide such as sodium iodide into the reaction mixtures. The iodine atom can reversibly exchange with the other halide atoms by an $S_N2$ mechanism thereby providing the most facile leaving group of these halides in the ether-forming transition state during the synthesis of the desired vinylarylmethylene ethers. The temperature is maintained below about 30 degrees Celsius) by occasional cooling, if necessary, over a period of 3 to 4 hours or until analytic monitoring (with use of MALDI-TOF MS, or other methods known to those skilled in the art) indicates that the etherification reactions are complete. Then stabilizers such as, for example, 0.2 g of 4-tert-butylcatechol (also known as 4-tert-butylpyrocatechol) (0.0012 mole) and 1 g (0.0013 mole) of 1,3,5-trimethyl-2,4,6-tris(3,5-di-(tert)-butyl-4-hydroxybenzyl)benzene, (also known as 3,3',3",5,5',5"-hexa-tert-butyl-alpha,alpha',alpha"-(mesitylene-2,4,6-triyl)tri-p-cresol and as IRGANOX 1330) are added and thoroughly mixed with the reaction products. The reaction products are supplied with an atmosphere of dried and filtered air. After suction filtration (if indicated), 1.5 L of ether is added and stirred for 30 min to remove pyridine salts and DMSO (if DMSO is present). The ether layer is removed by decantation. This is done 3 times. Then the ether is evaporated with stirring under an eluting current of dried and filtered air. After removal of the ether, 1 L of acetone is added, and stirred for 30 min before the acetone layer is decanted. This is done 3 times. Then stabilizers such as, for example, 0.2 g of 4-tert-butylcatechol (also known as 4-tert-butylpyrocatechol) (0.0012 mole) and 1 g (0.0013 mole) of 1,3,5-trimethyl-2,4,6-tris(3,5-di-(tert)-butyl-4-hydroxybenzyl)benzene, (also known as 3,3',3",5,5',5"-hexa-tert-butyl-alpha,alpha',alpha"-(mesitylene-2,4,6-triyl)tri-p-cresol and as IRGANOX 1330) are added and thoroughly mixed with the reaction products, because the stabilizers previously added might have been substantially removed by the extractive washings with ether and acetone. The reaction products are protected from light and concentrated to the desired extent by exposed to a stream of dried and filtered air.

Example 8

Derivatized cyclodextrins are prepared as follows. Into a mechanically stirred reaction vessel supplied with an eluting atmosphere of dried and filtered air, 567.49 g of recrystallized and dried beta-cyclodextrin (0.50 mole); 10.5 moles of pyridine; 0.50 mole of 4-dimethylaminopyridine (DMAP) [CAS Number 1122-58-3]; 0.50 mole of DBU (1,8-diazabicyclo[5.4.0]undec-7-ene); and a stabilizer such as 1,3,5-trimethyl-2,4,6-tris(3,5-di-(tert)-butyl-4-hydroxybenzyl)benzene, (also known as 3,3',3",5,5',5"-hexa-tert-butyl-alpha,alpha',alpha"-(mesitylene-2,4,6-triyl)tri-p-cresol, and as IRGANOX 1330); (0.167 mole) are placed. A minimal amount, if any, of DMSO (also known as dimethyl sulfoxide, methyl sulfoxide, sulfinylbismethane) is added only if needed to form a substantially homogenous fluid mixture or solution of these said ingredients that stirs easily or is capable of being stirred. Then with continued stirring, 4.00 moles of a vinylarylmethylenechloride is slowly added (with occasional cooling if necessary to maintain the temperature below about 30 degrees Celsius) over a period of 3 to 4 hours, or slowly heated to no more than about 50 degrees Celsius until analytic monitoring indicates that the etherification reactions are complete. Then with continued stirring, 6.50 moles of 6-bromohexanoic acid, dissolved in a minimal amount of DMSO to make a clear fluid solution, is added slowly (with occasional cooling if necessary to maintain the temperature below about 30 degrees Celsius) over a period of 3 to 4 hours, or slowly heated to no more than about 50 degrees Celsius until analytic monitoring indicates that the etherification reactions are complete. Then stabilizers such as, for example, 0.2 g of 4-tert-butylcatechol (also known as 4-tert-butylpyrocatechol) (0.0012 mole) and 1 g (0.0013 mole) of 1,3,5-trimethyl-2,4,6-tris(3,5-di-(tert)-butyl-4-hydroxybenzyl)benzene, (also known as 3,3',3",5,5',5"-hexa-tert-butyl-alpha,alpha',alpha"-(mesitylene-2,4,6-triyl)tri-p-cresol and as IRGANOX 1330) are added and thoroughly mixed with the reaction products. After suction filtration (if indicated), 1.5 L of ether is added and stirred for 30 min to remove pyridine salts and DMSO (if DMSO is present). The ether layer is removed by decantation. This is done 3 times. Then excess ether is evaporated with stirring under an eluting current of dried and filtered air, yet maintaining a fluid condition of the desired reaction products. Then, 1 L of acetone is added, and stirred for 30 min before the acetone layer is decanted. This is done 3 times. Then stabilizers such as, for example, 0.2 g of 4-tert-butylcatechol (also known as 4-tert-butylpyrocatechol) (0.0012 mole) and 1 g (0.0013 mole) of 1,3,5-trimethyl-2,4,6-tris(3,5-di-(tert)-butyl-4-hydroxybenzyl)benzene, (also known as 3,3',3",5,5',5"-hexa-tert-butyl-alpha,alpha',alpha"-(mesitylene-2,4,6-triyl)tri-p-cresol and as IRGANOX 1330) are added and thoroughly mixed with the fluid solution of the reaction products.

Example 9

N-vinylarylalkylene-N-phenylglycine, N-vinylarylalkylene-N-tolylglycine, N-vinylarylalkylene-N-methylglycine, or salts thereof are prepared by reacting N-phenylglycine, N-tolylglycine, and/or N-methylglycine with a vinylarylalkylenehalide, preferably in an aprotic solvent Example 10

Compositions containing one or more alpha-cyclodextrin, beta-cyclodextrin, and/or gamma-cyclodextrin are prepared by reacting vinylarylmethylene halides or vinylarylmethylene tosylates with one or more of those cyclodextrins dissolved in a solvent, preferably one ore more aprotic solvent (s), containing polymerization inhibitors or stabilizers and also containing a catalyst for bimolecular nucleophilic substitution ($S_N2$) reactions wherein hydroxyl groups of said cyclodextrins are transformed into nucleophilic, anionic, oxygen groups that can displace halides or tosylates from the vinylarylmethylene halides or tosylates, thereby forming stable ether linkages; and, by adjusting the proportions of the vinylarylmethylene halides or tosylates relative to the number of transformed hydroxyl groups of the cyclodextrins substantially all of the cyclodextrin molecules can be made to contain between one and a maximally obtainable number of covalently attached vinylarylmethylene ether groups; and likewise, by adjusting the proportions of vinylarylmethylene halides or tosylates relative to the number of (transformed) hydroxyl groups of the oligohydroxy compounds and reacting under similar conditions, vinylarylmethylene ethers of oligohydroxy compounds can be obtained with solubility parameters of substantially equal to the solubility parameters of the cyclodextrins containing covalently attached vinylarylmethylene ether groups; also to prevent gelation or premature polymerization during the foregoing preparative reactions, the polymerization inhibitors or stabilizers can comprise one or more member selected from the group typified by but not limited to 1,3,5-trimethyl-2,4,6-tris(3,5-di-(tert)-butyl-4-hydroxybenzyl)benzene, butylated hydroxytoluene, methyl sulfoxide, di-tert-butyl sulfide, and EDTA; after the syntheses, purification, and admixture of the forgoing; polymerization initiators can then be added, which comprise photoinitiators, chemical-cure initiators, or dual-cure polymerization initiators, as appropriate, that are selected from the group typified by those comprising phenyl bis(2,4,6-trimethylbenzoyl) phosphine oxide, camphorquinone, a salt, preferably a magnesium salt of N-vinylarylmethylene-N-phenylglycine, N-vinylarylmethylene-N-tolylglycine, or N-vinylarylmethylene-N-methylglycine, ethyl 4-dimethylaminobenzoate, diphenyliodonium hexafluorophosphate, benzoyl peroxide, N,N-dihydroxyethyl-para-toluidine, 4-dimethylamino phenethyl alcohol, 3-dimethylaminobenzoic acid, lithium para-toluenesulfinate, sodium para-toluenesulfinate, phenacylpyridinium oxalate, 1-phenacylpyridinium bromide, phenacyltriphenylphosphonium bromide, 3,3'-carbonylbis[7-(diethylamino)coumarin], meso-tetraphenylporphine, benzene-1,2,4,5-tetracarboxylic diimide, naphthalene diimide, 2,2'-azo-bis(amidinopropane) 2(HCl), N,N'-bis-vinlbenzyl-1,4,5,8-naphthalenediimide, and 2-benzoylmethylene-1-methyl-beta-naphthothiazoline.

It is thus seen that polymerizable compositions are provided, as are related kits and methods.

All references, including publications, patent applications, and patents, cited herein are hereby incorporated by reference. In any listing of possible ingredients or components, mixtures of the possible ingredients or components are contemplated unless expressly indicated otherwise. The description of certain embodiments as "preferred" embodiments, and other recitation of embodiments, features, or ranges as being preferred, is not deemed to be limiting, and the invention is deemed to encompass embodiments that are presently deemed to be less preferred. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention.

What is claimed is:

1. A composition that does not contain cyclodextrin derivatives, said composition comprising:
    hydrolytically stable, hydrophilic copolymerizable monomers comprising backbone moieties having two or more ether-linked vinylbenzyl groups,
    wherein said composition further comprises at least one hydrolytically stable, hydrophilic copolymerizable monomer having at least one ether-linked vinylbenzyl group and also one or more ether-linked adhesion-promoting groups selected from the group consisting of carboxyl-containing groups, amide-containing groups, amide-attached amino acid groups, amide-attached oligopeptide groups, and aldehyde-containing groups, wherein the linkage consists of from 1-16 carbon atoms, wherein said composition also contains at least one stabilizer and at least one polymerization initiator.

2. A composition that does not contain cyclodextrin derivatives, said composition comprising:
    hydrolytically stable, hydrophilic copolymerizable monomers comprising backbone moieties, and
    wherein said copolymerizable monomers contain one or more polymerizable vinylarylalkylene groups selected from the group consisting of para-vinylbenzyl, meta-vinylbenzyl, ortho-vinylbenzyl, 1-vinyl-naphthalene-4-methyl, 4-vinyl-3-chlorobenzyl, 2-vinyl-4-methoxybenzyl, 2-vinyl-4-phenoxybenzyl, ortho-methyl styrene, 1-methylene-2-vinylnaphthalene, 2-methylene-1-vinylnaphthalene, 1-methylene-5-vinylnaphthalene, and 2-vinyl-1-biphenylmethyl groups that are connected to their backbone moieties via ether linkages, and
    wherein said backbone moieties are selected from the group consisting of derivatized sugar alcohols, ethyleneglycol, diethyleneglycol, triethylene glycol, oligoethylene glycols, sorbitol, and other derivatized oligohydroxy compounds,
    wherein said copolymerizable monomers are further derivatized with substantially one or more ether-linked adhesion-promoting groups selected from the group consisting of undissociated carboxyl groups, dissociated anions of carboxyl groups, amides of carboxyl groups, amide-containing groups, amide-attached amino acid groups, ether-linked oligopeptide-containing groups, amide-attached oligopeptide groups, and aldehyde-containing groups,
    wherein said composition contains at least one stabilizer selected from the group consisting of di-tert-butyl sulfide, the monomethyl ether of hydroquinone, 4-tert-butylcatechol, butylated hydroxytoluene, butylated hydroxyanisole, 4-tert-butylcatechol, ascorbic acid, ascorbic acid salts, ascorbic acid anionic derivatives, 1,3,5-trimethyl-2,4,6-tris(3,5-di-t-butyl-4-hydroxybenzyl)benzene, ethylenediaminetetraacetic acid, salts of ethylenediaminetetraacetic acid, anionic derivatives of ethylenediaminetetraacetic acid, phytic acid, salts of phytic acid, anionic derivatives of phytic acid, oxalic acid, salts of oxalic acid, anionic derivatives of oxalic acid, citric acid, citric acid salts, and anionic derivatives of citric acid, wherein said composition contains at least one polymerization initiator, selected from the group consisting of phenylbis(2,4,6-trimethylbenzoyl)phosphineoxide, camphorquinone, camphorquinone-10-sulfonic acid, a salt of N-vinylarylalkylene-N-phenylglycine, a salt of N-vinylarylalkylene-N-tolylglycine, a salt of N-vinylarylalkylene-N-methylglycine, ethyl-4-dimethylaminobenzoate, diphenyliodoniumhexafluorophosphate, benzoyl peroxide, N,N-dihydroxyethyl-para-toluidine, 4-dimethylaminophenethylalcohol, 3-dimethylaminobenzoic acid, p-toluenesulfinic acid lithium salt, p-toluenesulfinic acid sodium salt hydrate, phenacylpyridiniumoxalate, 1-phenacylpyridinium bromide, phenacyltriphenylphosphonium bromide, 3,3'-carbonylbis[7-(diethylamino)coumarin], meso-tetraphenylporphine, benzene-1,2,4,5-tetracarboxylic diimide, naphthalene diimide, 2,2'-azo-bis(amidinopropane) 2(HCl), N,N'-bis-vinlbenzyl-1,4,5,8-naphthalenediimide, 2-benzoylmethylene-1-methyl-beta-naphthothiazoline, water-soluble derivatives thereof, and mixtures thereof.

3. A composition comprising hydrolytically stable, hydrophilic copolymerizable monomers, one or more stabilizer(s), and one or more polymerization initiator(s), wherein said composition does not contain cyclodextrin derivatives, wherein the copolymerizable monomers comprise backbone moieties selected from the group consisting of sorbitol (gulcitol), allitol (allodulcitol), epi-fucitol (6-deoxy-glucitol), meso-erythritol, dulcitol (galacitol), iditol (1,2,3,4,5,6-hexane hexol), perseitol (mannoheptitol), gulitol, gulonic gamma-lactone talitol (altritol, talaite), xylitol, ribitol, erythrose, allose, arabitol, galactose, gluco-heptose, glucomethylose (isorhamnose), glucose (dextrose), gulose, idose, isomalt, lactitol, mannitol (mannite, acritol), mannoheptose, mannose, maltitol, ribose, talose, xylose, epi-fucose (quinovose), psicose (allulose), idonic acid (2,3,4,5,6-pentahydroxy hexanoic acid), mannuronic acid, talonic acid, galacturonic acid, rhamnitol (rhamnite), ethyleneglycol, diethyleneglycol, triethyleneglycol, tetraethyleneglycol, poly(ethyleneglycol)(200), poly(ethyleneglycol)(400), poly(ethyleneglycol)(1000), and oligohydroxy compounds, and wherein the copolymerizable monomers comprise polymerizable vinylarylalkylene groups that are connected to their backbone moieties via ether linkages.

4. A composition according to claim 3 wherein said one or more stabilizer(s) is selected from the group consisting of 1,3,5-trimethyl-2,4,6-tris(3,5-di-t-butyl-4-hydroxybenzyl) benzene, di-tert-butyl sulfide, 4-tert-butylcatechol, butylated hydroxyanisole, ethylenediaminetetraacidic acid, ethylenediaminetetraacidic acid salts, ethylenediaminetetraacidic acid anionic derivatives, phytic acid, phytic acid salts, phytic acid anionic derivatives, oxalic acid, oxalic acid salts, oxalic acid anionic derivatives, citric acid, citric acid, citric acid salts, citric acid anionic derivatives, and mixtures thereof.

5. A composition according to claim 3, wherein said one or more polymerization initiator(s) is selected from the group consisting of diphenyliodoniumhexafluorophosphate, lithium para-toluenesulfinate, sodium para-toluenesulfinate, phenacylpyridinium oxalate, 1-phenacylpyridinium bromide, N,N-dihydroxyethyl-para-toluidine, henacyltriphenylphosphonium bromide, 3,3'-carbonylbis[7-(diethylamino)coumarin], meso-tetraphenylporphine, benzene-1,2,4,5-tetracarboxylic diimide, a salt of N-vinylarylmethylene-N-tolylglycine, 4-dimethylaminophenethylalcohol, 2-benzoylmethylene-1-methyl-beta-naphthothiazoline, 2,2'-azo-bis(amidinopropane) 2(HCl), and N,N'-bis-vinlbenzyl-1,4,5,8-naphthalenediimide.

6. A composition according to claim 3 wherein said copolymerizable monomers are prepared by reaction with a reagent selected from the group consisting of vinylbenzyl halide or tosylate, 1-vinyl-naphthalene-4-methyl halide or tosylate, 4-vinyl-3-chlorobenzyl halide or tosylate, 2-vinyl-4-methoxybenzyl halide or tosylate, 2-vinyl-4-phenoxybenzyl halide or tosylate, methyl styrene halide or tosylate, 1-methylene-2-vinylnaphthalene halide or tosylate, 2-methylene-1-vinylnaphthalene halide or tosylate, 1-methylene-5-vinylnaphthalene halide or tosylate, and 2-vinyl-1-biphenylmethyl halide or tosylate.

7. A composition according to claim 3 wherein said polymerizable vinylarylalkylene groups are selected from the group consisting of 1-vinyl-naphthalene-4-methyl, 4-vinyl-3-chlorobenzyl, 2-vinyl-4-methoxybenzyl, 2-vinyl-4-phenoxybenzyl, 1-methylene-2-vinylnaphthalene, 2-methylene-1-vinylnaphthalene, 1-methylene-5-vinylnaphthalene, and 2-vinyl-1-biphenylmethyl groups.

8. A composition according to claim 3 wherein said copolymerizable monomers are further derivatized with one or more aldehyde-containing groups through linkages to said backbone moieties having from 1-16 carbon atoms.

9. A composition according to claim 3 wherein said polymerizable vinylarylalkylene groups are selected from the group consisting of 1-vinyl-naphthalene-4-methyl, 4-vinyl-3-chlorobenzyl, 2-vinyl-4-methoxybenzyl, 2-vinyl-4-phenoxybenzyl, ortho-methyl styrene, 1-methylene-2-vinylnaphthalene, 2-methylene-1-vinylnaphthalene, 1-methylene-5-vinylnaphthalene, and 2-vinyl-1-biphenylmethyl groups.

10. A composition according to claim 3, wherein said one or more polymerization initiator(s) is selected from the group consisting of a photoinitiator, a chemical-cure initiator, and a dual-cure polymerization initiator.

11. A composition according to claim 3 wherein said hydrolytically stable, hydrophilic copolymerizable monomers are derivatized with two or more polymerizable vinylarylalkylene groups on substantially every molecule.

12. A composition according to claim 11 wherein said hydrolytically stable, hydrophilic copolymerizable monomers are derivatized by reaction with one or more reagent(s) selected from the group consisting of 2-haloacetic acid, 3-halopropionic acid, 4-halobutyric acid, 6-halohexanoic acid, 8-halooctanoic acid, 10-halodecanoic acid, 12-halododecanoic acid, 16-halohexadecanoic acid, 4-halobutanal, 5-halopentanal, 6-halohexanal, 6-(halomethyl)uracil, picolylhalide, 4-(halomethyl)benzoic acid, and 3-(halomethyl)benzoic acid.

13. A composition according to claim 3, said composition further comprising a reinforcing-effective amount of one or more reinforcing materials selected from the group consisting of solid particles and fibers.

14. A composition according to claim 13, wherein said one or more reinforcing materials comprises solid imogolite particles, the longest dimensions of which are predominately less than one micrometer and wherein said particles have been surface-treated with a mixture of silanes that consist essentially of equal parts of styrylethyltrimethoxysilane and octyltrimethoxysilane.

15. A composition according to claim 3, wherein said hydrolytically stable, hydrophilic monomers are selected from the group consisting of the vinylarylalkylene ethers of sorbitol, threitol, allitol, epi-fucitol, meso-erythritol, dulcitol, iditol, perseitol, gulitol, gulonic gamma-lactone, talitol, xylitol, erythrose, allose, galactose, gluco-heptose, gluco-methylose, glucose, gulose, idose, mannitol, mannoheptose, mannose, ribose, talose, xylose, epi-fucose, psicose, idonic acid, mannuronic acid, talonic acid, galacturonic acid, rhamnitol, tetraethyleneglycol, poly(ethyleneglycol)(200) tetrahydrofurfuryl alcohol, isobornyl alcohol, and mixtures thereof.

16. A composition according to claim 3 wherein said hydrolytically stable, hydrophilic copolymerizable monomers are free of hydrolysable ester [—C(=O)O—C—] linkages, and are biologically compatible or dentally compatible.

17. A composition according to claim 3, wherein said vinylarylalkylene groups are not susceptible to degradation that can occur from hydrolysis of ester linkages.

18. A composition according to claim 3, wherein said hydrolytically stable, hydrophilic monomers are prepared by reactions of sugar alcohols and oligohydroxy compounds with reagents selected from the group consisting of para-vinylbenzyl tosylate, meta-vinylbenzyl tosylate, ortho-vinylbenzyl tosylate, 1-vinyl-naphthalene-4-methyl tosylate (1-vinyl-4-methylenenaphthalene tosylate), 4-vinyl-3-chlorobenzyl tosylate, 2-vinyl-4-methoxybenzyl tosylate, 2-vinyl-4-phenoxybenzyl tosylate, 1-methylene-2-vinylnaphthalene tosylate, 2-methylene-1-vinylnaphthalene tosylate, 1-methylene-5-vinylnaphthalene tosylate, and 2-vinyl-1-biphenylmethyl halide or tosylate.

19. A composition according to claim 3 wherein said hydrolytically stable, hydrophilic copolymerizable monomers are selected from the group consisting of vinylarylalkylene ethers of oligohydroxy compounds wherein said copolymerizable monomers comprising two or more copolymerizable vinyl groups and wherein said composition is free of ester groups.

20. A composition according to claim 18, wherein said sugar alcohols and oligohydroxy compounds are selected from group consisting of sorbitol (gulcitol), allitol (allodulcitol), epi-fucitol (6-deoxy-glucitol), meso-erythritol, dulcitol (galacitol), iditol (1,2,3,4,5,6-hexane hexol), perseitol (mannoheptitol), gulitol, gulonic gamma-lactone talitol (altritol, talaite), xylitol, ribitol, erythrose, allose, arabitol, galactose, gluco-heptose, gluco-methylose (isorhamnose), glucose (dextrose), gulose, idose, isomalt, lactitol, mannitol (mannite, acritol), mannoheptose, mannose, maltitol, ribose, talose, xylose, epi-fucose (quinovose), psicose (allulose), idonic acid (2,3,4,5,6-pentahydroxy hexanoic acid), mannuronic acid, talonic acid, galacturonic acid, rhamnitol (rhamnite), ethyleneglycol, diethyleneglycol, triethyleneglycol, tetraethyleneglycol, poly(ethyleneglycol)(200), poly(ethyleneglycol)(400), poly(ethyleneglycol)(1000), glycerol, tetrahydrofurfuryl alcohol, isobornyl alcohol, 2-hydroxyethyl phosphate, 4-O-beta-D-galactopyranosyl-alpha-D-glucopyranose, beta-D-fructofuranosyl-alpha-D-glucopyranoside, methyl 4-O-beta-D-galactopyranosyl-alpha-D-glucopyranoside, alpha-cellotriose (O-beta-D-glucopyranosyl-(1-4)-O-beta-D-glucopyranosyl-(1-4)-alpha-D-glucopyranose), alpha-maltotriose, raffinose, and gentianose.

21. A composition according to claim 3, wherein said ether linkages are formed with the use of one or more catalysts selected from the group consisting of triethylamine, tripropylamine, tributylamine, N,N-dimethylbenzylamine, tribenzylamine, N,N,N',N'-tetramethyl-1,4-phenylenediamine, and sodium-tert-butoxide.

\* \* \* \* \*

UNITED STATES PATENT AND TRADEMARK OFFICE
CERTIFICATE OF CORRECTION

Page 1 of 1

PATENT NO. : 9,150,666 B2
APPLICATION NO. : 12/360421
DATED : October 6, 2015
INVENTOR(S) : Raphael L. Bowen et al.

It is certified that error appears in the above-identified patent and that said Letters Patent is hereby corrected as shown below:

In the Specification

The following should replace the paragraphs at Column 1, Lines 5 - 16:
STATEMENT OF FEDERALLY SPONSORED RESEARCH
This invention was made with government support under grant R01 DE005129 awarded by the National Institutes of Health. The government has certain rights in the invention.

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*